US012678127B1

(12) United States Patent
Tek

(10) Patent No.: US 12,678,127 B1
(45) Date of Patent: Jul. 14, 2026

(54) CONTRAST AND B-MODE COMBINATION FOR STRAIN ANALYSIS IN MEDICAL ULTRASOUND IMAGING

(71) Applicant: Siemens Medical Solutions USA, Inc., Malvern, PA (US)

(72) Inventor: Huseyin Tek, Princeton, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 19/058,289

(22) Filed: Feb. 20, 2025

(51) Int. Cl.
*A61B 8/08* (2006.01)
*A61B 8/00* (2006.01)

(52) U.S. Cl.
CPC .......... *A61B 8/0883* (2013.01); *A61B 8/0858* (2013.01); *A61B 8/463* (2013.01); *A61B 8/481* (2013.01); *A61B 8/485* (2013.01); *A61B 8/5223* (2013.01); *A61B 8/5253* (2013.01); *A61B 8/5284* (2013.01); *A61B 2576/023* (2013.01)

(58) Field of Classification Search
CPC ..... A61B 8/0883; A61B 8/0858; A61B 8/481; A61B 8/485; A61B 8/5223; A61B 2576/023
See application file for complete search history.

(56) References Cited

U.S. PATENT DOCUMENTS

| | | | |
|---|---|---|---|
| 7,773,787 | B2 | 8/2010 | Tek et al. |
| 9,129,417 | B2 | 9/2015 | Zheng et al. |
| 10,373,700 | B2 | 8/2019 | Sharma et al. |
| 2007/0249912 | A1 | 10/2007 | Tek |
| 2008/0100621 | A1 | 5/2008 | Aharon et al. |
| 2014/0058715 | A1 | 2/2014 | Sharma et al. |

OTHER PUBLICATIONS

"Combination of contrast-enhanced wall motion analysis and myocardial deformation imaging during dobutamine stress echocardiography" by A.I. Nagy et al. Euro Heart J—Cardio Imag. 16, 88-95. 2015.*

* cited by examiner

*Primary Examiner* — Jason M Ip

(57) ABSTRACT

For boundary detection, such as heart wall detection for strain or another quantification, the boundary is detected using multiple types of imaging, such as B-mode and contrast. The confidence in the detected locations is used to form a more accurate boundary, such as replacing low confidence locations from B-mode imaging with higher confidence locations from the contrast imaging. Even where experts may struggle to identify boundaries, a more accurate boundary is created and used by the image processor or processing.

10 Claims, 3 Drawing Sheets

100A — Acquire B-mode

100B — Acquire Contrast

110A — Detect Wall Locations

110B — Detect Wall Locations

120A — Determine Confidence in Locations

120B — Determine Confidence in Locations

130 — Align Contrast and B-mode based on Good Locations

140 — Combine Locations using Confidences

150 — Calculate Strain

160 — Fuse B-mode and Contrast

170 — Display Strain, Boundary, and/or Fused Image 200    202    210    212

CONTRAST AND B-MODE COMBINATION FOR STRAIN ANALYSIS IN MEDICAL ULTRASOUND IMAGING

BACKGROUND

The present embodiments relate to medical ultrasound imaging. Ultrasound imaging is used to assess global and regional myocardial muscle and motion mechanics from B-mode echocardiography data. Myocardium boundaries are determined at end of systole and end of diastole. These detected boundary representations are used to compute ejection fraction and global strain for quick assessment of global function of heart chambers. The local analysis of myocardium wall motion relies on a motion field of the speckle at the detected boundaries. However, the local measurements may not be reliable.

Contrast agents are commonly imaged, so that both contrast images and B-mode images may be reviewed to assist in visualization and quantification. Contrast echocardiography imaging microbubble agents may be helpful in increasing the accuracy of diagnosis and for enhancing interpreter confidence. In general, contrast enhanced echocardiography images capture endo-cardium boundaries and their motion well, if acquired timely. However, like B-mode, contrast images also have some quality issues. For example, parts of the endo-cardium wall may not be highlighted accurately due to the acquisition timings or turbulent nature of flow. In addition, accurate localization of annulus regions may be difficult in contrast images, thus, basal segment boundaries are difficult to detect and track, even by experts. The full myocardium wall may not be visible in contrast images.

SUMMARY

By way of introduction, the preferred embodiments described below include methods, systems, computer readable media, and instructions for boundary detection, such as heart wall detection for strain or another quantification. The boundary is detected using multiple types of imaging, such as B-mode and contrast. The confidence in the detected locations is used to form a more accurate boundary, such as replacing low confidence locations from B-mode imaging with higher confidence locations from the contrast imaging. Even where experts may struggle to identify boundaries, a more accurate boundary is created and used by the image processor or processing.

In a first aspect, a method is provided for quantification of heart wall performance with a medical ultrasound system. An image processor detects heart wall locations for each B-mode image in a sequence of B-mode images of a patient and determined first confidence measures for the heart wall locations from the sequence of the B-mode images. The image processor also detects the heart wall locations for each contrast image in a sequence of contrast images of the patient and determines second confidence measures in the heat wall locations from the sequence of the contrast images. The image processor generates a heart wall boundary for each of different times from the heart wall locations from the sequence of B-mode images, the heart wall locations from the sequence of contrast images, the first confidence measures, and the second confidence measures. The image processor calculates and displays a strain from the heart wall boundary for multiple of the different times.

In a second aspect, a method is provided for boundary detection of a heart wall with a medical ultrasound system. Locations of the heart wall detected from B-mode imaging by an ultrasound scanner are combined with locations of the heart wall detected from contrast imaging by the ultrasound scanner into a heart wall boundary. The locations for the heart wall boundary are selected in the combining based on confidence in the locations. The heart wall boundary and/or a strain calculated from the heart wall boundary are displayed.

In a third aspect, a system is provided for contrast and B-mode combination. A transmit beamformer is configured to cause the transducer to transmit first pulses for B-mode imaging and second pulses for contrast agent imaging. A receive beamformer is configured to form B-mode signals responsive to the first pulses and contrast agent signals responsive to the second pulses. An image processor is configured to detect heart wall locations over time from the B-mode signals, to detect the heart wall locations over time from the contrast signals, and to replace the heart wall locations from the B-mode signals with the heart wall locations from the contrast signals based on relative confidence. A display is configured to display an image based on the heart wall locations detected from the B-mode signals with the replacement heart wall locations from the contrast signals.

Any one or more of the aspects, approaches, or concepts summarized above or in the Illustrative Embodiments below may be used alone or in combination. The aspects or concepts described for one Illustrative Embodiment or aspect may be used in other embodiments or aspects. The aspects or concepts described for a method or system may be used in others of a system, method, or non-transitory computer readable storage medium.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the FIGURES are not necessarily to scale, emphasis instead being placed upon illustrating the principles of the invention. Moreover, in the FIGURES, like reference numerals designate corresponding parts throughout the different views.

DETAILED DESCRIPTION OF THE DRAWINGS AND PRESENTLY PREFERRED EMBODIMENTS

Until now, contrast enhanced and B-Mode echo are analyzed independently for assessing heart wall performance of a patient. Now, the B-mode and contrast boundary detection may be combined. The combination may use confidence assigned for each location on the boundary. The confidence is used to combine, allowing accurate merging of results from the contrast and B-mode imaging. High quality boundary segments from multiple sources are combined. The detected and tracked myocardium wall may be fused with contrast data for improved understanding of wall motion.

By combining contrast enhanced echo data with B-Mode data, improved global and/or regional strain computations are provided. A segmented ventricle from contrast may be fused with the B-mode to show blood flow with the myocardium wall as well as valves. Segmented wall tissue may be fused with contrast to show tissue in flow imaging. Improved visualization is provided from the higher quality boundary. Rather than separately reviewing B-mode and contrast imaging for diagnosis, information from both are provided together in a single and simpler report.

Figures 1, 2:
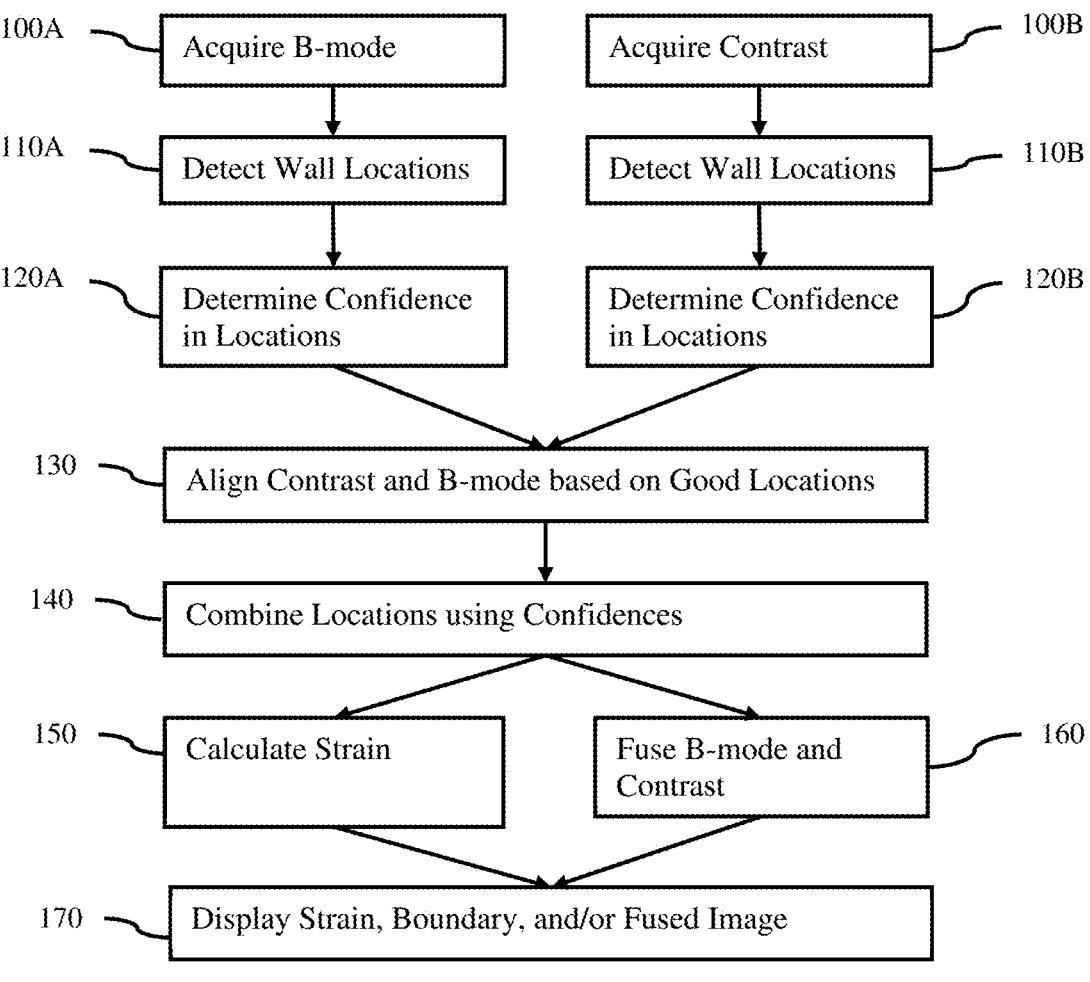
FIG. 1 is a flow chart diagram of one embodiment of a method for boundary detection and/or quantification of heart wall performance with a medical ultrasound system.
FIG. 2 illustrates example B-mode and contrast images.

FIG. 1 shows one embodiment of a method for boundary detection and/or quantification of wall performance with a medical ultrasound scanner. For example, automated strain quantification is provided using a boundary formed from locations detected from contrast and B-mode imaging. Strain quantification may be performed independently for contrast and B-mode, where some of the boundary from B-mode uses contrast locations and/or some of the boundary from contrast uses B-mode locations. The boundary or boundaries are formed using confidence in the detected locations form these multiple sources.

Figure 5:
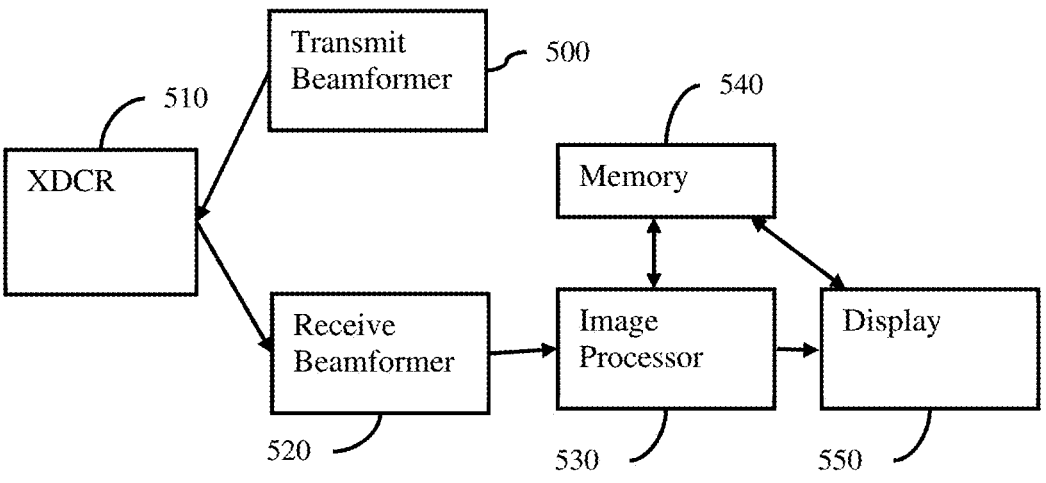
FIG. 5 shows is a block diagram of one embodiment of a medical ultrasound system for boundary detection and/or wall performance quantification.

The method is implemented by the system of FIG. 5 or a different system. An ultrasound scanner, such as a medical diagnostic ultrasound scanner, images a field of view for contrast agent imaging and B-mode imaging in act 100. Alternatively, the B-mode and contrast data are acquired by an image processor from memory and/or transfer over a computer network for act 100. The image processor performs acts 110-160. A display, based on an image generated by the image processor, performs act 170. Other devices may perform any of the acts, such as controller, server, workstation, or computer operating as a medical ultrasound system.

The method is performed in the order shown (top to bottom or numerical) or a different order. For example, act 100A is performed simultaneously with, before, or after any of acts 100B, 110B, and/or 120B. As another example, act 100B is performed simultaneously with, before, or after any of acts 100A, 110A, and/or 120A. As another example, acts 150 and 160 are performed simultaneously or in any order (e.g., act 150 before or after act 160).

Additional, different, or fewer acts may be provided. For example, acts 100A and 100B are not performed. As another example, acts 130, 150, and/or 160 are not performed. In another example, act 170 is not performed, such as where the quantification and/or ultrasound image are transferred to another computer or system or stored in memory. As yet another example, acts for configuring the ultrasound scanner and/or using the output are provided.

In acts 100A and 100B, an ultrasound scanner acquires B-mode and contrast images. The patient is scanned to acquire a sequence of B-mode images over one or more heart beats. The same patient is also scanned to acquire a sequence of contrast images over one or more heart beats. The B-mode and contrast imaging may be sequential, such as B-mode scanning, then injecting contrast agents, and then contrast scanning. Simultaneous or interleaved scanning may be used. In alternative implementations, the B-mode and/or contrast images are acquired by loading from memory or transfer over a computer network.

The B-mode images and contrast images are of a same view of the patient. For example, A2C, A4C, A3C or other standardized heart images are acquired. For volume imaging, one or more particular chambers or tissue walls are included in the scanned volume.

Images include echocardiography data (signals) representing different spatial locations in the patient. The images may be data (scan data) used to create an image or a created image. The image may be a two-dimensional or a three-dimensional representation of the patient. For example, a plane or area of the patient is scanned. As another example, a volume is scanned.

Any B-mode imaging may be used. The intensity of returned echoes is imaged. The medical ultrasound scanner images a field of view of a patient.

Any contrast agent imaging may be used. Contrast agents are introduced into a patient. The contrast agents are microbubbles. A transducer probe is used to transmit and receive acoustic energy for imaging the field of view and/or contrast agents in the field of view. Acoustic beams with a lower power are transmitted along the scan lines of a region, and echoes responsive to the acoustic beams are received. The lower power is provided by a mechanical index of 0.7 or lower, lower frequency waveforms, smaller aperture, slower pulse repetition frequency, combinations thereof, or another beam characteristic.

The region scanned includes contrast agents or an area that may include contrast agents. The contrast agents respond to ultrasound energies. A given imaging frame of data may include information from contrast agents. The information may also include response from tissue or fluids. Data is acquired at each spatial location of a region of interest in each frame of data.

The imaging is of contrast agents, so includes contrast agent detection. The intensity of contrast agent response to the acoustic energy is determined. Any contrast agent imaging mode may be used. In one embodiment, the response from contrast agents is obtained at a cubic fundamental of ultrasound signals. For example, ultrasound signals are transmitted in a plurality of pulses having at least two different amplitude levels and phases. Received signals responsive to the transmissions are combined. In other embodiments, harmonic imaging is used. By transmitting at one frequency range and detecting response at a harmonic (e.g., second harmonic or twice the transmit frequencies), contrast agents' response may be greater than tissue response. In one embodiment, a B-mode detector and corresponding B-mode detection is used for both contrast agent and tissue information (B-mode) detection. Alternatively, a separate detector, such as Doppler or other detector, is used to detect contrast agent information.

A sequence of frames of data (images) is generated for each of B-mode data and contrast data. The sequence may be substantially continuous or periodic (e.g., acquired once or more every heart cycle). The B-mode and contrast sequences each includes frames of data representing a scanned region at different times. Each frame of data represents a same or overlapping region. Any number of images or frames are acquired over one or more heart beats, such as 6-20 frames per heartbeat.

In acts 110A and 110B, the image processor detects tissue wall locations. Any tissue wall may be detected. For example, heart wall locations are detected. As another example, endo-cardium and/or epi-cardium boundaries are detected.

Any sampling of the tissue wall may be used. N contour points are detected for each image. For example, 10-40 locations along a chamber in 2D are detected. As another example, 50-100 locations over a 3D surface are detected. The locations are evenly spaced or may be based of landmarks. A contour in 2D or 3D is detected for each frame in a heart cycle. Contours as sampled points (locations) are detected over the sequence of B-mode images and the sequence of contrast images.

A machine-learned model detects the locations. For example, a neural network is trained in one instance to detect the locations of the heart wall from input B-mode images, and a neural network is also trained in another instance to detect the locations of the heart wall from contrast images. The neural networks of both contrast and B-mode instances use a same architecture. Alternatively, different architectures or models are used for contrast and B-mode. Any neural network may be used, such as an image-to-image, encoder-decoder, U-Net or other arrangement receiving an image or images as input and outputting detected locations (e.g., contour or contours).

The same or different machine-learned model is used to detect for the different images or frames through the sequence. For example, the same or different machine-learned models are applied for wall detection in end-diastole and end-systole images. The machine-learned models may be used for detecting in images at other times.

In other implementations, thresholding, random walker, template matching, model matching, and/or other pro-grammed border detection is applied. Instead of using a machine-learned model, the locations are found by optimization, fitting, or other approach.

In one example, the locations (e.g., endo-cardium bound-ary) are detected by a machine-learned model in the end-diastole and end-systole images by the image processor for both contrast and B-mode sequences. For B-mode, the epi-cardium boundary may also be detected. In other approaches, other boundaries are instead or additionally detected.

After detection in the end-systole and end-diastole images, the locations are tracked through the contrast and B-mode sequences. For example, speckle tracking (e.g., Lagrangian particle tracking) is used to track locations through the images in B-mode. Landmark-based, line shape, or other boundary tracking may be used to track locations through images in contrast. The tracking may be from the end-diastole image to other images of the sequence. The tracking may be from end-systole or both end-systole and end-diastole in other approaches. As an alternative to track-ing, detection is performed for each image in each of the sequences. Different approaches may be used for the differ-ent sequences.

The detection, using detection per image and/or tracking for some images, provides a motion trajectory through each sequence for each of the locations. The motion over time of each location through the sequence is determined. The constructed motion trajectory indicates the wall motion, such as for computing segmental strains. The segment may correspond to any portion of the wall, such as portions formed by one or more locations.

The same location in a B-mode image may be the same or different position than the location in the contrast image. Due to differences in detection and/or differences in the contrast verses B-mode image, the detection of a location may be in a different or the same position.

In acts 120A and 120B, the image processor determines confidence for the detected locations (e.g., heart wall loca-tions). The confidence of each location in each of the images through a sequence is determined. The confidence may instead be by location through the sequence, such as one confidence measure being determined for each of the sample locations through the sequence. Confidences are measured for the locations forming the contour for the B-mode sequence and the contrast sequence.

Due to the poor image segments or errors in detection (e.g., in tracking), parts of detected and tracked contours may not correspond to true myocardium boundaries. True boundary points are determined by assigning confidence measures to motion trajectories of myocardium boundary points and classifying them as true motion, if possible. Alternatively, the confidence measure is for the detected position for a given time. The determination of confidence is separate for the contrast and B-mode-based locations, pro-viding separate confidence values for the separate B-mode contour and contrast contour despite being for the same part of the wall.

The image processor determines the confidence in a detected location for one time or over the sequence. One or more machine-learned models, such as a neural network formed as a classifier, are applied to the detected locations, image for the location, and/or other information to output a confidence. In one embodiment, the machine-learned model outputting the detected location also outputs a confidence in the location being correct. Where different machine-learned models are used for contrast and B-mode, then the different machine-learned models separately output the confidences in detection for the locations for B-mode and contrast.

Alternatively, the motion trajectory is analyzed or mea-sured to indicate the confidence. For example, the motion trajectory over the sequence for a location is fit to a model of motion, measured for local continuity, and/or measured for global continuity. The fit may indicate a similarity or other measure showing how close the motion trajectory is to an expected trajectory. Any feature matching of the motion trajectory to expected motion may be used. The continuities indicate a level of smoothness. The motion trajectory is expected to have a gradual or smooth change over time. Alternatively, a machine-learned model outputs a confidence in response to input of the motion trajectory.

In one implementation, the myocardium boundary is represented by equally spaced N control points where N is between 20 and 40 for the left ventricle chamber. The tracking algorithm propagates these control points from an initial boundary (e.g., contour samples detected in an end-diastole image) at the initial time to all corresponding tissue points in all other times, thus, creating motion field or N motion trajectories. The motion trajectory of the myocar-dium is a 1D curve in a three-dimensional space (i.e., $T(x,y,f)$ where x and y represents spatial location and f is the frame number or time) or four-dimensional space (I.e., $T(x,y,z,f)$ where z is another spatial dimension).

Each trajectory point is assigned with a confidence mea-sure based on data and path regularity. In addition, or alternatively, one or more quality measures are assigned to the whole curve (trajectory) and/or different segments (parts of the trajectory). For example, it may be possible that a full quality measure may be low, but trajectory segments with high quality may still exist. Specifically, it is common that certain speckles may not be visible in B-mode echo data for many times due to the inherent issues of ultrasound acqui-sition systems or due to the experience level of the sonog-rapher. Thus, visualization of regional mechanics, such as strains, should specifically highlight regions where compu-tations come from unverified trajectories or data.

The confidence measure, $C(i,t)$, for each point on a motion trajectory is determined from model fit, local continuity, and global continuity:

$$C(i, t) = \text{Fit}(i, t)^* Cl(i, t)^* Cg(i, t)$$

where Fit(i,t) measures how well data in the current location resembles the initial speckle or boundary model, CI measures the local continuity of trajectory, and Cg measures the global continuity of continuity of trajectory. The global continuity may use motion priors obtained from detected contours at certain frames to measure the level of continuity, such as a measure of similarity to an expected motion. The function is calculated. Alternatively, a machine-learned model may indicate the Fit, CI, Cg, or C in response to input of the motion trajectory and indication of the location. Clustering may be used to determine the confidence for a location, segment, and/or globally.

Each of the locations is labeled. A confidence is provided for each location. The same confidence may be used for a given location over time, or separate confidence values are provided for the same location over time (i.e., in each frame). More than one confidence may be provided for each location, such as a global, segment, and/or location specific confidence values.

The confidence may be used to determine whether the location is a true boundary point. Where the confidence is above a threshold, then the detected location is considered accurate or part of a true boundary. Conversely, any confidence value below the threshold represents possibly inaccurate positioning (location detection). Combinations of multiple values of confidence for a location may be used to determine the accuracy. Alternatively, multiple thresholds are used, one for each measure of confidence for a location. By being above the threshold for each confidence measure, the detected location is indicated as true. One or more values below the respective threshold indicate possible inaccurate location.

Figure 3:
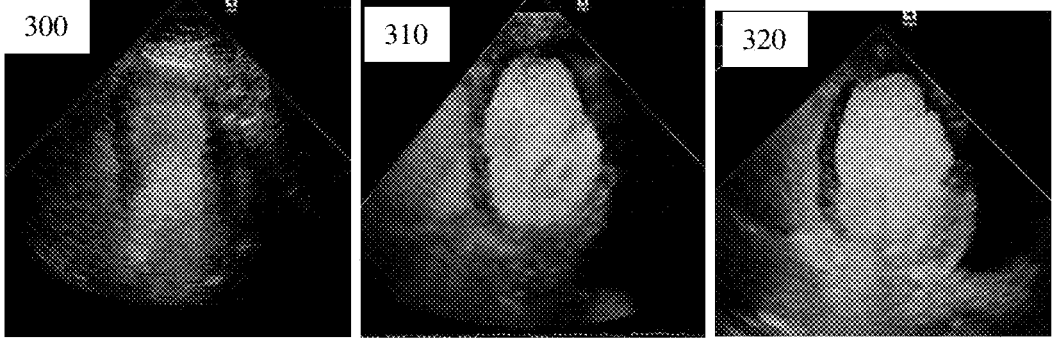
FIG. 3 illustrates example contrast images.

FIG. 2 shows two B-mode images 200, 202 where detection of the myocardium wall motion may be difficult. Two contrast images 210, 212 are examples where the endocardium wall motion may be captured in good detail. Thus, the accuracy or confidence in detection of endocardium locations in the contrast sequence may be above a threshold, and the accuracy or confidence in detection of the myocardium locations in the B-mode sequence may be below a threshold. FIG. 3 shows contrast images 300, 310, and 320 where detection of the endo-cardium may be difficult for tracking algorithms and/or experts. Thus, the accuracy or confidence in detection of the endo-cardium locations in the contrast sequence may be below a threshold.

In act 130, the image processor aligns the B-mode and contrast images. The alignment is a spatial and/or temporal alignment.

For temporal alignment, the heart cycle timing relative to each image is determined. Using EKG and/or data analysis, the heart cycle relative to the images of each sequence may be identified. With two sequences, the images of each sequence may be temporally aligned or offset. The temporal relationship of each image to the heart cycle allows temporal alignment of the images of one sequence to the images of the other sequence. Interpolation, extrapolation, and/or modeling may optionally be used to create images at the same times in the heart cycle for further temporal alignment.

For spatial alignment, any rigid or non-rigid (deformation) transformation or alignment may be used. Images of different sequences from the same or similar times are spatially aligned. For example, landmarks are detected. The deformation to align or register the landmarks to be at the same positions in two images is determined, such as using a physics model, statistical shape model, or other modeling.

In one implementation, the detected locations of the wall are used as the landmarks. The B-mode and contrast images are aligned based on the heart wall locations for the B-mode images and the heart wall locations for the contrast images. Further accuracy in registration or alignment is provided by using the confidence measures for the locations. Only locations with a confidence in the accuracy of the location above a threshold in both images are used for registration. The locations used for the alignment are selected based on the confidence. The contrast and B-mode data are aligned by computing the optimal transformation between the true (threshold confidence) boundary points of contrast and B-mode data. Once true myocardium boundary points are determined for both contrast and B-mode, these images are aligned by using the wall locations as landmarks (i.e., landmark based registration algorithms are applied to determine the transformation).

Once the wall locations are spatially aligned, the locations from the different types of images are combined using the confidence in act 140. Locations of the heart wall detected from B-mode imaging by an ultrasound scanner are combined with locations of the heart wall detected from contrast imaging by the ultrasound scanner into a heart wall boundary or refined locations. Similarly, locations of the heart wall detected form contrast imaging by the ultrasound scanner are combined with locations of the heart wall detected from B-mode imaging by the ultrasound scanner into a heart wall boundary or refined locations. A heart wall boundary or contour based on contrast updated with B-mode locations and a separate heart wall boundary or contour based on B-mode updated with contrast locations are generated. Alternatively, one heart wall boundary or contour based on both B-mode and contrast locations is generated.

The locations for the heart wall boundary are selecting in the combining based on confidence in the locations. Poorly tracked and/or detected contour points in one type of data, such B-mode, can be replaced with the good ones from the other types, such as contrast, after applying appropriate transformation obtained from the registration. For example, the locations of the heart wall detected from the B-mode imaging are used unless the confidence for the locations from the B-mode imaging is below a threshold. For the locations below the confidence threshold, the locations of the heart wall detected from the contrast imaging are used, at least where the confidence for the locations from the contrast imaging is above the threshold.

Figure 4:
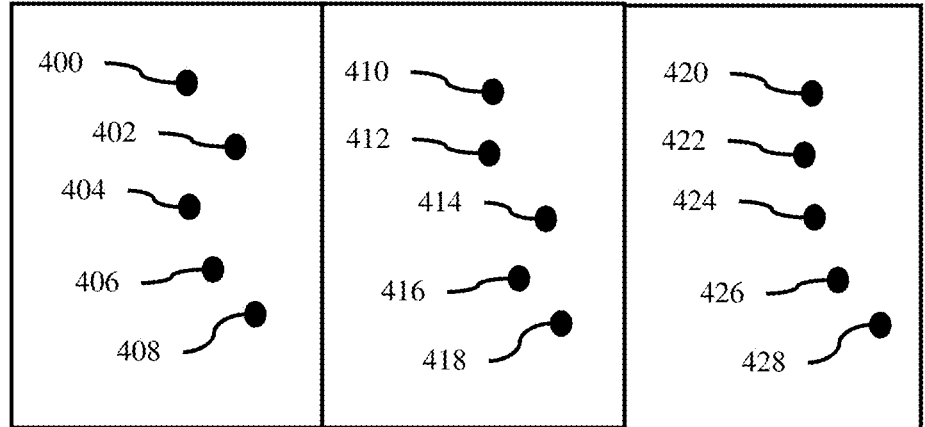
FIG. 4 illustrates location determination from B-mode, contrast, and combined.

FIG. 4 shows an example. A segment of a heart wall is represented by five boundary points or location. Locations 400-408 are from B-mode. Locations 410-418 are from contrast. The locations 400-408 are for the same parts of the wall as locations 410-418. For the boundary formed from B-mode, the locations 400, 404, 406, and 408 have confidence above the threshold, and the location 402 has a confidence below the threshold. For location 402, the same location identified by the registration or alignment is examined in the contrast data, location 412. Location 412 has confidence above the threshold, so the location 412 may replace the location 402. As a result, locations 420, 424, 426, and 428 correspond or are locations 400, 404, 406, and 408. Location 422 is location 412. The low confident boundary points from motion trajectories of B-mode data are corrected by using high confident boundary points of contrast data, when available.

In a similar example, for the contrast boundary, locations 410, 412, 416, and 418 have confidence above the threshold, so are used (corresponding to locations 420, 422, 426, and 428, respectively). Location 414 has confidence below the threshold, so the corresponding B-mode location 404 is examined. Since corresponding location 404 has a confidence in detection above the threshold, location 424 corresponds to location 404. The low confident boundary points from motion trajectories of contrast data are corrected by using high confident boundary points of B-mode data, when available.

In another implementation, the locations of both the contrast and B-mode boundaries are examined. The highest confidence location for each part of the wall is selected. This forms one boundary from both B-mode and contrast without default to B-mode or contrast.

Where only low confidence location are available, then that location may be used with a low confidence detection or is not used. The locations with low confidence may be labeled, such as allowing display to indicate locations or regions of the wall detected only with low confidence.

The image processor generates a heart wall boundary for each of different times from the heart wall locations from the sequence of B-mode images, the heart wall locations from the sequence of contrast images, the confidence measures of the B-mode locations, and the confidence measures of the contrast locations. This is done using the B-mode locations primarily (i.e., replacing low confidence B-mode and keeping high confidence B-mode), using the contrast locations primarily (i.e., replacing low confidence contrast and keeping high confidence contrast), and/or using the highest confidence from B-mode and contrast. For example, for each heart wall location from the B-mode images, the confidence measure for each location detected in B-mode is compared to a threshold. When the confidence measure is below the threshold, the heart wall location from the B-mode images is replaced with the heart wall location from the contrast images where the confidence measure in the contrast location is above the threshold.

The replacement may be by location in each image. In another approach, the replacement is by location through the sequence. For example, where the motion trajectory is examined for confidence, the confidence may reflect a global confidence in the location through the sequence. The replacement is of that location through the entire sequence (e.g., 10 images in a sequence, so the location in all 10 images is replaced by the location through the sequence detected in the other type of imaging). Any time window may be used for the replacement, such as identifying confidence by part of the heart cycle, so replacing locations in that part.

Similarly, spatial replacement may be by individual sample point or by segment. The confidence measures for multiple locations may be combined to identify from which source (e.g., B-mode or contrast) the locations for the segment should be used.

In act 150, the image processor computes a strain from the heart wall boundary for multiple of the different times. The boundary or locations from a sequence are used. The locations may include one or more locations replaced from another source (e.g., B-mode location replaced by contrast location). The strain is calculated from the boundary locations as combined in act 140.

Any strain may be calculated. For example, one or more local and/or global strains are calculated. For local strain, the strain may be calculated for one or more segments. Each segment may be represented by one or more locations. The strain for the entire heart cycle (e.g., end-diastole to end-systole) and/or over part of the cycle may be calculated. The B-mode boundary, with one or more replaced locations from contrast, is used to calculate the strain, but the contrast boundary or combination boundary may be used instead. Separate strains may be calculated for the same period and location but from different boundaries (e.g., calculate from contrast boundary and calculate from B-mode boundary).

The change in heart wall boundary length over time provides the strain. The amount of expansion and/or contraction between different times indicates the strain. Other measures of strain may be used. Other quantifications using the boundary may be performed, such as ejection fraction. Where the boundary is in three dimensions, quantification (e.g., strain) for a surface or cross-sectional area or a volume of the wall or chamber may be performed.

In act 160, the image processor fuses tissue information from the B-mode images with flow information from the contrast images into one or more heart images. The fusing uses one or more masks based on the heart wall boundary or boundaries. For example, tissue information from the B-mode imaging is fused with flow information from the contrast imaging. The heart wall boundary separates the tissue information and the flow information, so a mask is provided to select the data (B-mode or contrast) to use for each location.

In addition to improved tracking, important features of each type of data may be fused with the other type. For example, it is possible to segment the myocardium wall from the detected and tracked endo and epi layers. The B-mode data (speckle data) inside this myocardium mask may be fused to contrast data by using the already computed transformations. One image may be formed from contrast with overlaid or replaced tissue information from B-mode. Similarly, blood flow inside the ventricle may be segmented to form a ventricle mask with the flow. This flow may then be fused with the B-mode. One image may be formed from B-mode with overlaid or replaced ventricle flow from contrast. Alternatively, an image is formed by combining the B-mode data for tissue locations using the boundary and flow or blood pool locations from contrast.

In act 170, the strain or strains are displayed. The image processor generates an image of the strain. The strain is represented graphically, as an annotation, with alphanumeric text, and/or color or scale. The image is displayed, such as by a display screen or printer.

The strain or strains may be displayed with other information in the image. For example, the boundary (e.g., locations, segments formed from locations, a fit line or curve, and/or another boundary display) is shown for a given time or as a video (e.g., sequence from different times) with the strain overlaid as an annotation. B-mode and/or contrast images may be displayed, such as displaying a B-mode image and a contrast image, with the boundaries in both, and strain annotation. Any heart image may be displayed with the strain.

In one implementation, the heart wall boundary is displayed without or with the strain. The heart wall boundary is displayed as a fit line or curve to the locations, but other representations (e.g., the locations without a fit line) may be used. The heart wall boundary at one time or multiple times (e.g., end-diastole and end-systole) is displayed alone or overlaid on a B-mode or contrast image. A sequence of images may display the heart wall boundary over time, such as showing a video of change in the heart wall boundary.

For the image of the heart, a fused image formed from both contrast and B-mode data may be displayed. The fused image shows the tissue information from the B-mode imaging and the blood pool or flow information from the contrast imaging. The fused image or sequence of fused images is displayed with or without the boundary and/or strain. B-mode only and/or contrast only images of the heart may be displayed.

FIG. 5 shows a system for contrast and B-mode combination. Imaging data and/or detected wall locations are fused. The system implements the method of FIG. 1 or another method.

The system includes a transmit beamformer 500, a transducer 510, a receive beamformer 520, an image processor 530, a memory 540, and a display 550. Additional, different, or fewer components may be provided. For example, the image processor 530 is separate from the data flow for imaging. As another example, a scan converter or other backend processor is provided. In yet another example, the transmit beamformer 500, transducer 510, and/or receive beamformer 520 are not provided, such as where the ultrasound imaging system is a computer or server operating on images stored in the memory 540.

The system is a medical diagnostic ultrasound imaging system in one embodiment, but other imaging systems of the same (ultrasound) or different modality may be used. In other embodiments, part or all the system is implemented in a computer or workstation. For example, previously acquired frames of data are processed without the beamformers 500, 520 or transducer 510.

The transmit beamformer 500 is an ultrasound transmitter, memory, pulser, analog circuit, digital circuit, or combinations thereof. The transmit beamformer 500 is configured by settings, hardware, firmware, and/or software to generate waveforms for a plurality of channels with different or relative amplitudes, delays, and/or phasing. Upon transmission of acoustic waves from the transducer 510 in response to the generated waveforms, one or more beams are formed. The transmit beamformer 500 may cause the beam to have a particular phase and/or amplitude. For example, the transmit beamformer 500 transmits a sequence of pulses associated with a given scan line or to adjacent scan lines. The pulses correspond to beams with different amplitudes and/or relative phases. In alternative embodiments, a single beam is used for any given scan line and/or beams with a same amplitude and/or relative phases are used.

A controller or the image processor 530 configures the transmit beamformer 500 for causing the transducer 510 to transmit pulses for B-mode imaging and pulses for contrast agent imaging. Any B-mode and/or contrast mode scanning may be used.

For B-mode imaging, pulses are transmitted to generate echoes from tissue. Any scan format and pulse arrangement for B-mode imaging may be used.

For imaging contrast agents, acoustic energy with a lower mechanical index (MI) is generated. For example, acoustic energy of 0.7 MI or lower is used to limit or avoid destruction of contrast agents. The pulses of acoustic energy cause less contrast agent destruction and are used to measure echo or response of the contrast agents to the transmitted acoustic energy. Acoustic energy with higher MI, such as associated with destruction of contrast agents, may also be used for imaging contrast.

The transducer 510 is a 1-, 1.25-, 1.5-, 1.75- or 2-dimensional array of elements. The transducer 510 includes a plurality of elements for transducing between acoustic and electrical energies. The elements are piezoelectric or capacitive membrane-based structures. The elements connect with channels of the transmit and receive beamformers 500, 520.

The receive beamformer 520 is configured by firmware, hardware, and/or software to form receive beams sampling the scan region in response to transmitted beams. The receive beamformer 520 includes a plurality of channels with amplifiers, delays, and/or phase rotators, and one or more summers. Each channel connects with one or more transducer elements. The receive beamformer 520 applies relative delays, phases, and/or apodization to form one or more receive beams in response to each imaging transmission. The focused information from the channels is summed dynamically. In alternative embodiments, the receive beamformer 520 is a processor for generating samples using Fourier or other transforms.

The receive beamformer 520 may include a filter, such as a filter for isolating information at a second harmonic or other frequency band relative to the transmit frequency band. Such information may more likely include desired tissue, contrast agent, and/or flow information. In another embodiment, the receive beamformer 520 includes a memory or buffer and a filter or adder. Two or more receive beams are combined to isolate information at a desired frequency band, such as a second harmonic, cubic fundamental, or another band.

Any desired sequence of transmit and receive operation may be used to obtain ultrasound information (beamformed samples or signals). The receive beamformer 520 is configured to form B-mode signals responsive to some pulses and contrast agent signals responsive to the other pulses. Pulses may be used for both contrast and B-mode scanning.

B-mode data may be obtained by scanning a region once and detecting the intensity of any response. B-mode may be used for tissue and/or contrast agent imaging. Correlation or motion tracking may be used to derive fluid information from B-mode data. B-mode operation may provide contrast agent information, such as by filtering to isolate information at a second harmonic. Doppler information may be obtained by transmitting sequences of beams along each scan line. A corner turning memory may be used to isolate tissue, contrast agents, and/or flow information from Doppler signals. Other now known or later developed modes may be used.

In one embodiment, the B-mode scanning is separate from but may be interleaved with a contrast agent-imaging mode. Contrast agent information is information primarily responsive to contrast agents, and tissue information is information primarily responsive to tissue. Isolating information at the second, even, odd, sub, or other harmonics may more likely identify information from contrast agents. For example, a two-pulse technique is used. The pulses have a same amplitude, but different phase. By summing the response, information associated with even harmonics is identified. Filtering may alternatively be used. Alternatively, or additionally, relative phasing is provided in the receive processing.

In one embodiment, the transmit sequence is controlled to generate echo signals responsive to the cubic fundamental. The beamformer 500 is operable to transmit a plurality of pulses having at least two different amplitude levels and at least two of the plurality of pulses having opposite or different phases. Transmitter power may be varied in any suitable manner, as for example by adjusting the voltage applied to individual transducer elements or by adjusting the number of transducer elements (or transmit aperture) used to form a particular pulse.

The image processor 530 is a B-mode detector, Doppler detector, pulsed wave Doppler detector, correlation processor, Fourier transform processor, application specific integrated circuit, general processor, control processor, field programmable gate array, digital signal processor, analog circuit, digital circuit, combinations thereof, or other now known or later developed device for detecting contrast agent and/or tissue information from beamformed ultrasound samples, forming a boundary, and displaying and/or quantifying with the boundary. In one embodiment, the image processor 530 includes a B-mode detector, Doppler estimator, and/or contrast imager in parallel tracks. For example, the B-mode detector operates on the same or different beamformed samples to detect tissue response. The contrast imager operates on beamformed samples to detect contrast agent response. Any image processor for detecting contrast agent and/or tissue information may be used, such as a single detector. Another part of the image processor, such as a general processor, detections locations and generates outputs from the detected locations.

The image processor 530 outputs frames of ultrasound data or signals. The frames of data are formatted in an acquisition format (e.g., polar coordinate), a display format (e.g., scan converted into a Cartesian coordinate format or an image), or another format. Each frame of data is an image that represents a one, two, or three-dimensional scanned region. The frames of data include a single or multiple types of data. For example, one frame of data includes just contrast agent information. As another example, one frame of data includes contrast agent information for some spatial locations and another type of information (e.g., B-mode or Doppler) for other spatial locations. Different types of data may be provided in the same frame for a same spatial location. In another example, the different types of data are provided in different frames of data.

In an alternative embodiment, the image processor 530 loads data from a network or memory 540. For example, DICOM or other images are loaded. Each image is a frame of data. One frame may include different types of data, one overlaid on another. Alternatively, each frame includes only one type of data with different frames for different data types.

The image processor 530 is configured by software, firmware, and/or hardware design. The image processor 530 is configured to combine B-mode and contrast data, such as detecting a heart wall using both B-mode, contrast, and confidence information.

In one implementation, the image processor 530 is configured to detect heart wall locations over time from the B-mode signals, to detect the heart wall locations over time from the contrast signals, and to replace the heart wall locations from the B-mode signals with the heart wall locations from the contrast signals and/or vice versa based on relative confidence. The relative confidence may be by selecting the location with a highest confidence. The relative confidence may instead use comparison to one or more thresholds, where confidence below the threshold indicates a location to be replaced with a location corresponding to a confidence above the threshold. For example, where a confidence measure for a location of the heart wall location from the B-mode is below a threshold and a confidence measure for the location from the contrast signal is above the threshold, the location from the contrast signal is used.

The image processor 530 is configured to detect locations of a wall independently in a sequence of frames of data (signals), such as detecting in B-mode sequence and a contrast sequence independently. The detection may use a machine-learned model or other process. Tracking may be used to detect over time (i.e., through the sequence).

The image processor 530 is configured to determine the confidence in the accuracy of the detected locations. For example, a machine-learned model used to detect a location also outputs a confidence. As another example, the motion trajectory of the location through all or part of a sequence is analyzed. A measurement (e.g., fit or similarity to model or motion prior, local continuity, and/or global continuity) of the motion trajectory over time indicates the confidence.

The image processor 530 may be configured to align the B-mode signals with the contrast agent signals. The alignment uses the locations from the B-mode signals, the locations from the contrast signals, and measures of confidence in the locations from the B-mode signals and the contrast signals. Detected wall locations with confidence above a threshold in both B-mode signals and contrast signals are used as landmarks for registration (transformation or alignment).

The image processor 530 is configured to determine the boundary and then use the boundary for imaging and/or calculation, such as strain calculation and fusion of imaging. The image processor 530 is configured to generate an image showing the detected boundary formed from replaced locations, fused B-mode and contrast image formed using one or more masks based on the detected boundary, and/or strain or other calculation based on the detected boundary.

The display 550 is a CRT, monitor, LCD, flat panel, projector, printer, or other display device. The display 550 receives display values for displaying an image. The display values are formatted as a one-dimensional image, two-dimensional image, or three-dimensional representation. The image is based on heart wall locations detected from B-mode signal or contrast signals with replacement locations from the other of contrast signal or B-mode signal. The image is of the formed boundary, fused information based on masking using the boundary, and/or strain or other quantification of or using the boundary (e.g., change in boundary over time).

The memory 540 is a buffer, random access memory, read only memory, cache, hard drive, removable, optical, flash, system memory, combinations thereof, or other now known or later developed device for frames of data, images, and/or instructions. The memory 540 may be a combination of different memory devices or separately addressed regions. In one embodiment, the memory 540 stores data to be used, during use, or after processing for the processor 530.

The image processor 530 operates pursuant to instructions. A computer readable storage medium stores data representing instructions executable by one or both of these programmed processors. The instructions for implementing the processes, methods and/or techniques discussed herein are provided on computer-readable storage media or memories 540, such as a cache, buffer, RAM, removable media, hard drive, or other computer readable storage media. Computer readable storage media include various types of volatile and nonvolatile storage media. The functions, acts or tasks illustrated in the FIGURES or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code, and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

Listed below are various Illustrative Embodiments. The Illustrative Embodiments summarize different combinations of aspects. Other combinations of any of the aspects with any other one or more of the aspects may be provided. Aspects from one type (e.g., method or system) may be used in another type (system or method).

Illustrative Embodiment 1. A method for quantification of heart wall performance with a medical ultrasound system, the method comprising: detecting, by an image processor, heart wall locations for each B-mode image in a sequence of B-mode images of a patient; determining, by the image processor, first confidence measures for the heart wall locations from the sequence of the B-mode images; detecting, by the image processor, the heart wall locations for each contrast image in a sequence of contrast images of the patient; determining, by the image processor, second confidence measures in the heat wall locations from the sequence of the contrast images; generating, by the image processor, a heart wall boundary for each of different times from the heart wall locations from the sequence of B-mode images, the heart wall locations from the sequence of contrast images, the first confidence measures, and the second confidence measures; calculating, by the image processor, a strain from the heart wall boundary for multiple of the different times; and displaying the strain.

Illustrative Embodiment 2. The method of Illustrative Embodiment 1, wherein detecting the heart wall locations in the sequence of B-mode images comprises detecting endo-cardium boundary and epi-cardium boundary locations by a first machine-learned model; and wherein detecting the heart wall locations in the sequence of contrast images comprises detecting the endo-cardium boundary locations by a second machine-learned model.

Illustrative Embodiment 3. The method of Illustrative Embodiment 2, wherein determining the first confidence measures comprises receiving the first confidence measures from the first machine-learned model; and wherein determining the second confidence measures comprises receiving the second confidence measures from the second machine-learned model.

Illustrative Embodiment 4. The method of any of Illustrative Embodiments 1-3, wherein detecting the heart wall locations in the sequence of B-mode images comprises detecting the heart wall locations in an end-systole image of the B-mode images and an end-diastole image of the B-model images and tracking the heart wall locations for images of the B-mode images between the end-systole and end-diastole images; and wherein detecting the heart wall locations in the sequence of contrast images comprises detecting the heart wall locations in an end-systole image of the contrast images and an end-diastole image of the contrast images and tracking the heart wall locations for images of the contrast images between the end-systole and end-diastole images.

Illustrative Embodiment 5. The method of any of Illustrative Embodiments 1-4, wherein determining the first and second confidence measures comprise determining the first and second confidence measures as measures of a motion trajectory for each of the heart wall locations.

Illustrative Embodiment 6. The method of Illustrative Embodiment 5, wherein determining the first and second confidence measures comprises determining with the measures of the motion trajectory comprising fit to a model of motion, local continuity, and/or global continuity.

Illustrative Embodiment 7. The method of any of Illustrative Embodiments 1-6, further comprising aligning the B-mode and contrast images based on the heart wall locations for the B-mode images, the heart wall locations for the contrast images, the first confidence measures, and the second confidence measures; and then performing the generating.

Illustrative Embodiment 8. The method of any of Illustrative Embodiments 1-7, wherein generating comprises, for each heart wall location from the B-mode images, testing the first confidence measure to a threshold, and when the first confidence measure is below the threshold, replacing the heart wall location from the B-mode images with the heart wall location from the contrast images where the second confidence measure is above the threshold.

Illustrative Embodiment 9. The method of any of Illustrative Embodiments 1-8, further comprising: fusing tissue information from the B-mode images with flow information from the contrast images into one or more heart images, the fusing using one or more masks based on the heart wall boundary; and displaying the one or more heart images with the strain.

Illustrative Embodiment 10. The method of any of Illustrative Embodiments 1-9, wherein calculating the strain comprise calculating a local or global strain from a change in the heart wall boundary between the different times.

Illustrative Embodiment 11. A method for boundary detection of a heart wall with a medical ultrasound system, the method comprising: combining locations of the heart wall detected from B-mode imaging by an ultrasound scanner with locations of the heart wall detected from contrast imaging by the ultrasound scanner into a heart wall boundary, the locations for the heart wall boundary selecting in the combining based on confidence in the locations; and displaying the heart wall boundary and/or a strain calculated from the heart wall boundary.

Illustrative Embodiment 12. The method of Illustrative Embodiment 11, wherein combining comprises using the locations of the heart wall detected from the B-mode imaging unless the confidence for the locations from the B-mode imaging is below a threshold, and then instead using the locations of the heart wall detected from the contrast imaging where the confidence for the locations from the contrast imaging is above the threshold.

Illustrative Embodiment 13. The method of any of Illustrative Embodiments 11-12, further comprising determining the confidences for the locations from the B-mode imaging and the locations from the contrast imaging by one or more machine-learned models and/or measuring motion trajectories of each location of the locations over time.

Illustrative Embodiment 14. The method of any of Illustrative Embodiments 11-13, further comprising aligning the B-mode imaging and the contrast imaging based on the locations detected from the B-mode imaging and the locations detected from the contrast imaging, the locations used in the aligning selected based on the confidence.

Illustrative Embodiment 15. The method of any of Illustrative Embodiments 11-14, further comprising fusing tissue information from the B-mode imaging with flow information from the contrast imaging where the heart wall boundary separates the tissue information and the flow information; and wherein displaying further comprises displaying an image or images of the fused tissue information and flow information with display of the heart wall boundary and/or the strain.

Illustrative Embodiment 16. A system for contrast and B-mode combination, the system comprising: a transducer; a transmit beamformer configured to cause the transducer to transmit first pulses for B-mode imaging and second pulses for contrast agent imaging; a receive beamformer configured to form B-mode signals responsive to the first pulses and contrast agent signals responsive to the second pulses; an image processor configured to detect heart wall locations over time from the B-mode signals, to detect the heart wall locations over time from the contrast signals, and to replace the heart wall locations from the B-mode signals with the heart wall locations from the contrast signals based on relative confidence; and a display configured to display an image based on the heart wall locations detected from the B-mode signals with the replacement heart wall locations from the contrast signals.

Illustrative Embodiment 17. The system of Illustrative Embodiment 16, wherein the image processor is configured to replace where a confidence measure for a location of the heart wall locations from the B-mode signals is below a threshold and a confidence measure for the location from the contrast signal is above the threshold.

Illustrative Embodiment 18. The system of any of Illustrative Embodiments 16-17, wherein the image processor is configured to align the B-mode signals with the contrast agent signals using the locations from the B-mode signals, the locations from the contrast signals, and measures of confidence in the locations from the B-mode signals and the contrast signals.

Illustrative Embodiment 19. The system of any of Illustrative Embodiments 16-18, wherein the image comprises a strain.

Illustrative Embodiment 20. The system of any of Illustrative Embodiments 16-19, wherein the relative confidence is from one or more machine-learned models or measurement of motion trajectory over time.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for quantification of heart wall performance with a medical ultrasound system, the method comprising:

detecting, by an image processor, heart wall locations for each B-mode image in a sequence of B-mode images of a patient;

determining, by the image processor, first confidence measures for the heart wall locations from the sequence of the B-mode images;

detecting, by the image processor, the heart wall locations for each contrast image in a sequence of contrast images of the patient;

determining, by the image processor, second confidence measures in the heat wall locations from the sequence of the contrast images;

generating, by the image processor, a heart wall boundary for each of different times from the heart wall locations from the sequence of B-mode images, the heart wall locations from the sequence of contrast images, the first confidence measures, and the second confidence measures;

calculating, by the image processor, a strain from the heart wall boundary for multiple of the different times; and displaying the strain.

2. The method of claim 1, wherein detecting the heart wall locations in the sequence of B-mode images comprises detecting endo-cardium boundary and epi-cardium boundary locations by a first machine-learned model; and wherein detecting the heart wall locations in the sequence of contrast images comprises detecting the endo-cardium boundary locations by a second machine-learned model.

3. The method of claim 2, wherein determining the first confidence measures comprises receiving the first confidence measures from the first machine-learned model; and wherein determining the second confidence measures comprises receiving the second confidence measures from the second machine-learned model.

4. The method of claim 1, wherein detecting the heart wall locations in the sequence of B-mode images comprises detecting the heart wall locations in an end-systole image of the B-mode images and an end-diastole image of the B-model images and tracking the heart wall locations for images of the B-mode images between the end-systole and end-diastole images; and wherein detecting the heart wall locations in the sequence of contrast images comprises detecting the heart wall locations in an end-systole image of the contrast images and an end-diastole image of the contrast images and tracking the heart wall locations for images of the contrast images between the end-systole and end-diastole images.

5. The method of claim 1, wherein determining the first and second confidence measures comprise determining the first and second confidence measures as measures of a motion trajectory for each of the heart wall locations.

6. The method of claim 5, wherein determining the first and second confidence measures comprises determining with the measures of the motion trajectory comprising fit to a model of motion, local continuity, and/or global continuity.

7. The method of claim 1, further comprising aligning the B-mode and contrast images based on the heart wall locations for the B-mode images, the heart wall locations for the contrast images, the first confidence measures, and the second confidence measures; and then performing the generating.

8. The method of claim 1, wherein generating comprises, for each heart wall location from the B-mode images, testing the first confidence measure to a threshold, and when the first confidence measure is below the threshold, replacing the heart wall location from the B-mode images with the heart wall location from the contrast images where the second confidence measure is above the threshold.

9. The method of claim 1, further comprising:

fusing tissue information from the B-mode images with flow information from the contrast images into one or more heart images, the fusing using one or more masks based on the heart wall boundary; and displaying the one or more heart images with the strain.

10. The method of claim 1, wherein calculating the strain comprise calculating a local or global strain from a change in the heart wall boundary between the different times.

* * * * *